United States Patent [19]

Lee

[11] Patent Number: 4,955,468
[45] Date of Patent: Sep. 11, 1990

[54] SEPARATION OF HYDROCARBON MIXTURES

[75] Inventor: Fu M. Lee, Bartlesville, Okla.

[73] Assignee: Phillips Petroleum Company, Bartlesville, Okla.

[21] Appl. No.: 404,799

[22] Filed: Sep. 8, 1989

[51] Int. Cl.$^5$ .............................................. B01D 3/40
[52] U.S. Cl. ....................................... 203/53; 203/14; 203/58; 203/70; 585/865; 585/867
[58] Field of Search .................... 203/14, 53, 70, 58, 203/43, 91, 95; 585/865, 867

[56] References Cited

U.S. PATENT DOCUMENTS

| | | | |
|---|---|---|---|
| 2,508,723 | 5/1950 | Mayland et al. | 585/866 |
| 2,679,472 | 5/1954 | Tooke | 203/60 |
| 2,695,322 | 11/1954 | Weedman | 585/839 |
| 2,736,755 | 2/1956 | Reuter et al. | 55/84 |
| 2,771,494 | 11/1956 | Weedman | 585/836 |
| 2,786,804 | 3/1957 | Nelson | 203/60 |
| 2,809,925 | 10/1957 | Nelson | 203/60 |
| 2,839,452 | 6/1958 | Nelson | 203/60 |
| 2,846,485 | 8/1958 | Meason et al. | 585/866 |
| 2,891,894 | 6/1959 | Cier et al. | 203/60 |
| 2,949,422 | 8/1960 | Grimes | 208/321 |
| 3,034,969 | 5/1962 | Makin, Jr. | 203/60 |
| 3,193,489 | 7/1965 | Gemmell | 208/80 |
| 3,301,911 | 1/1967 | Boatright | 585/252 |
| 3,349,009 | 10/1967 | Ruehlen | 203/67 |
| 3,591,490 | 7/1971 | Müller et al. | 208/313 |
| 3,723,256 | 3/1973 | Thompson | 203/43 |
| 3,860,496 | 1/1975 | Ginnasi et al. | 203/28 |
| 3,884,769 | 5/1975 | Mikitenko et al. | 203/96 |
| 4,053,369 | 10/1977 | Cines | 203/52 |
| 4,134,795 | 1/1979 | Howat, III | 203/53 |
| 4,278,505 | 7/1981 | Danulat et al. | 203/59 |
| 4,401,517 | 8/1983 | Lee | 203/53 |
| 4,514,262 | 4/1985 | Berg | 203/51 |
| 4,661,209 | 4/1987 | Berg | 203/57 |
| 4,690,733 | 9/1987 | Forte et al. | 203/21 |
| 4,746,420 | 5/1988 | Darian et al. | 208/222 |

OTHER PUBLICATIONS

"Extractive Distillation Saves Energy", by Ian Sucksmith, Chemical Engineering, Jun. 29, 1982, pp. 91–95.
"Handbook of Separation Techniques for Chem. Engineers", by Philip Schweitzer, McGraw Hill Book Co., 1979, pp. 1-135 to 1-143.
"Perry's Chemical Engineers' Handbook", 6th Edition, McGraw Hill Book Co., 1984, pp. 13-53 to 13-57.
"The Essentials of Extraction", by J. L. Hemphrey et al., Chemical Engineering, Sep. 17, 1984; pp. 84–87.
"Kirk-Othmer Encyclopedia of Chemical Technology", Third Edition, vol. 9, John Wiley and Sons, Inc., 1980, pp. 693–716.

Primary Examiner—Virginia Manoharan
Attorney, Agent, or Firm—K. K. Brandes

[57] ABSTRACT

An extractive distillation process for separating at least one cycloalkane or aromatic hydrocarbon from at least one close-boiling alkane employs as solvent at least one N-mercaptoalkyl-2-pyrrolidone, preferably N-($\beta$-mercaptoethyl)-2-pyrrolidone, either alone or in admixture with about 0.1–10 weight-% water.

A liquid-liquid extraction process for separating at least one cycloalkane or aromatic hydrocarbon from at least one alkane employs as solvent at least one N-mercaptoalkyl-2-pyrrolidone, preferably N-($\beta$-mercaptoethyl)-2-pyrrolidone, either alone or in admixture with about 0.1–10 weight-% water.

28 Claims, 1 Drawing Sheet

SEPARATION OF HYDROCARBON MIXTURES

BACKGROUND OF THE INVENTION

In one aspect, this invention relates to the separation of saturated cycloaliphatic hydrocarbons (cycloalkanes, naphthenes) from close-boiling paraffinic hydrocarbons (alkanes, paraffins) by extractive distillation. In another aspect, this invention relates to the separation of cycloalkanes from alkanes by liquid-liquid extraction. In still another aspect, this invention relates to the separation of aromatic hydrocarbons from close-boiling alkanes by extractive distillation. In a further aspect, this invention relates to the separation of aromatic hydrocarbons from alkanes by liquid-liquid extraction.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91–95, the disclosure of which is herein incorporated by reference. Other literature sources on extractive distillation techniques include the "Handbook of Separation Technques for Chemical Engineers" by Philip A. Schweitzer, McGraw-Hill Book Company, 1979, pages 1–135 to 1–143; and Perry's Chemical Engineers Handbook, 6th Edition, McGraw-Hill Book Company 1984, pages 13–53 to 13–57, the disclosures of which are herein incorporated by reference.

The separation of naphthenes (cycloparaffins), in particular cyclohexane, from close-boiling paraffins (alkanes) by extractive distillation is known and has been described in the patent literature, such as in U.S. Pat. Nos. 2,508,723; 2,771,494; 2,846,485; 2,891,894; 3,034,969 and 4,053,369, the entire disclosures of which are herein incorporated by reference. The separation of aromatics from close-boiling alkanes by extractive distillation is described in U.S. Pat. Nos. 3,591,490 and 4,278,505, the entire disclosures of which are herein incorporated by reference. However, there is an ever present need to develop more selective solvents than those presently known in the extractive distillation of mixtures of close-boiling paraffins and naphthenes and/or aromatics. In particular, it is highly desirable to develop improved extractive distillation processes for producing cyclohexane of high purity, which is a starting material for making nylon and other useful polymeric materials.

The separation of aromatic and non-aromatic hydrocarbons by liquid-liquid extraction is also well known, and has been described in the patent literature, e.g. in U.S. Pat. Nos. 2,949,422 and 3,193,489, the entire disclosures of which are herein incorporated by reference. However, there is a present need to use more effective solvents for such liquid-liquid extraction processes.

SUMMARY OF THE INVENTION

It is an object of this invention to provide a process for separating cycloalkanes (naphthenes) from close-boiling alkanes (paraffins) by extractive distillation employing a novel solvent (extractant). It is another object of this invention to produce cyclohexane of high purity from a mixture comprising cyclohexane and close-boiling isoparaffins (i.e., isoparaffins having nearly the same volatility as cyclohexane) by extractive distillation employing a novel solvent (extractant). It is a further object of this invention to provide an extractive distillation process for separating aromatic hydrocarbons from close-boiling alkanes. It is still another object of this invention to separate aromatic hydrocarbons from alkanes by liquid-liquid extraction. It is a still further object of this invention to separate cycloalkanes from alkanes by liquid-liquid extraction. Other objects and advantages will be apparent from the detailed description of the invention and the appended claims.

In accordance with this invention, in a process for separating at least one cycloalkane (naphthene) containing 5–10 carbon atoms per molecule from at least one close-boiling alkane (paraffin), i.e., one alkane or a plurality of alkanes having nearly the same boiling point at atmospheric pressure conditions as said cycloalkane, by extractive distillation of a feed comprising (preferably consisting essentially of) said at least cycloalkane and said at least one alkane, the improvement is to use a solvent (also referred to as extractant or entrainer) consisting essentially of at least one N-mercaptoalkyl-2-pyrrolidone, in particular N-($\beta$-mercaptoalkyl)-2-pyrrolidone, wherein the mercaptoalkyl group contains 1–5 carbon atoms per molecule. In a preferred embodiment, the feed cycloalkane is cyclohexane. In another preferred embodiment, the solvent is N-($\beta$-mercaptoethyl)-2-pyrrolidone. In a further preferred embodiment, the solvent consists essentiallyof said at least one N-mercaptoalkyl-2-pyrrolidone and about 0.1–10 weight-% water.

Also in accordance with this invention, in a process for separating at least one aromatic hydrocarbon containing 6–10 carbon atoms per molecule from at least one close-boiling paraffin by extractive distillation of a feed comprising (preferably consisting essentially of) said at least one aromatic hydrocarbon and said at least one close-boiling paraffin, the improvement is to use a solvent consisting essentially of at least one N-mercaptoalkyl-2-pyrrolidone, as defined above, preferably N-($\beta$-mercaptoethyl)-2-pyrrolidone. In another embodiment, the solvent consists essentially of said at least one N-mercaptoalkyl-2-pyrrolidone and about 0.1–10 weight-% water.

Further in accordance with this invention, in a process for separating at least one aromatic hydrocarbon containing 6–18 carbon atoms per molecule from at least one alkane containing 5–20 carbon atoms per molecule by liquid-liquid extraction of a feed comprising (preferably consisting essentially of) said at least one aromatic hydrocarbon and said at least one alkane, the improvement is to use a solvent (extractant) consisting essentially of at least one N-mercaptoalkyl-2-pyrrolidone, as defined above, wherein an extract phase is formed which comprises said solvent and at least a portion of said at least one aromatic feed hydrocarbon, and a raffinate phase is formed in which the concentration of said at least one aromatic hydrocarbon is lower than the concentration of said at least one aromatic hydrocarbon in the feed. In another embodiment, the solvent consists essentially of said at least one N-mercaptoalkyl-2-pyrrolidone and about 0.1-10 weight-% water.

Still further in accordance with this invention, in a process for separating at least one cycloalkane containing 6-18 carbon atoms per molecule from at least one alkane containing 5-20 carbon atoms per molecule by liquid-liquid extraction of a feed comprising (preferably consisting essentially of) said at least one cycloalkane and said at least one alkane, the improvement is to use a solvent consisting essentially of N-mercaptoalkyl-2-pyrrolidone, as defined above, wherein an extract phase is formed which comprises said solvent and at least a portion of said at least one feed cycloalkane, and a raffinate phase is formed in which the concentration of said at least one cycloalkane is lower than the concentration of said at least one cycloalkane in the feed. In another embodiment, the solvent consists essentially of said at least one N-mercaptoalkyl-2-pyrrolidone and about 0.1-10 weight-% water.

DETAILED DESCRIPTION OF THE INVENTION

Extractive Distillation

Figure 1:
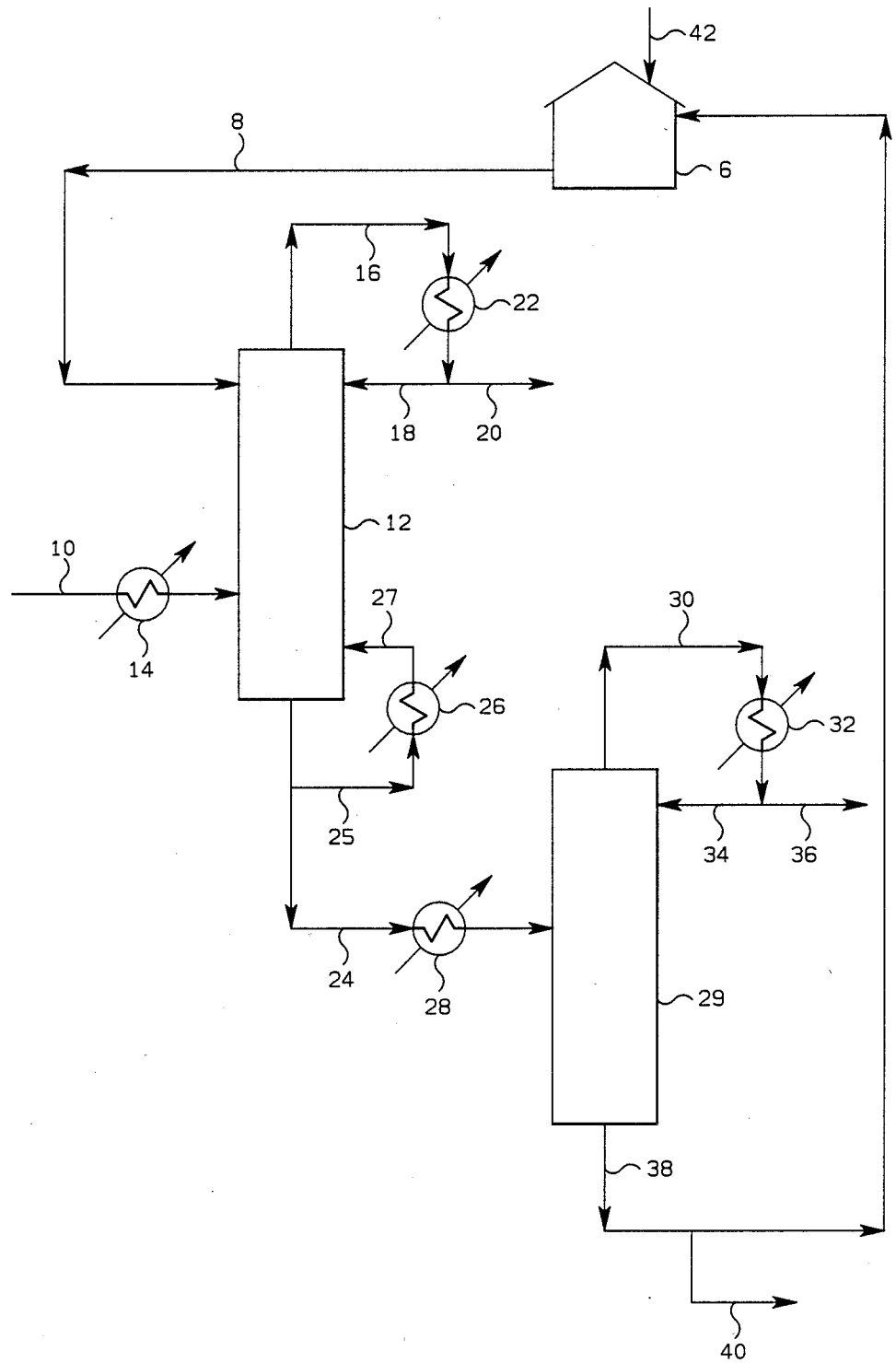
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

In the first embodiment of this invention, any hydrocarbon feed which contains at least one cycloalkane (naphthene) containing 5-10 carbon atoms per molecule and at least one close-boiling alkane (preferably containing 5-10 carbon atoms per molecule, more preferably branched alkane or isoparaffin) can be used in the first extractive distillation process of this invention. Preferably, the boiling point (at atmospheric pressure conditions, i.e., at about 1 atm.) of the cycloalkane(s) and alkane(s) to be separated by extractive distillation is in the range of from about 80° to about 350° F., more preferably about 100°-300° F. Generally, the boiling points of the cycloalkane(s) and the alkane(s) differ by about 0.2°-10° F. (preferably about 0.5°-5° F.), at about 1 atm.

Preferably, the cycloalkane content in the feed is about 30-95 weight-% (more preferably about 75-90 weight-%), and the alkane content is about 5-70 weight-% (more preferably about 10-25 weight-%). Preferably, this feed is essentially free of aromatics.

Non-limiting examples of cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cyclooctane, and the like and mixtures thereof. Presently preferred is cyclohexane.

Non-limiting examples of alkanes are n-pentane, n-hexane, 2-methylpentane, 3-methylpentane, n-heptane, 2,2-dimethylpentane, 2,4-dimethylpentane, 3,3-dimethylpentane, 2,3-dimethylpentane, 2-methylhexane, 3-methylhexane, 2,2,3-trimethylbutane, n-octane, 2-methyloctane, n-nonane, and the like, and mixtures thereof.

In the second embodiment of this invention, any hydrocarbon feed which contains at least one aromatic hydrocarbon containing 6-10 carbon atoms per molecule and at least one close-boiling alkane (preferably containing 6-10 carbon atoms per molecule) can be used in the second extractive distillation process of this invention. Boiling points and boiling point differences are about the same for these aromatics/alkane feeds as for the above-described cycloalkane/alkane feeds. Preferably, the content of aromatic hydrocarbons is about 10-95 weight-% (more preferably about 20-80 weight-%), and the alkane content is about 5-90 weight-% (more preferably about 20-80 weight-%). Preferably, this feed is essentially free of cycloalkanes.

Non-limiting examples of suitable aromatic hydrocarbons are benzene, toluene, meta-, ortho- and para-xylenes, ethylbenzene, trimethylbenzenes, methylethylbenzenes, and the like, and mixtures of the above. Preferred aromatic hydrocarbons are benzene, toluene and the xylenes. Non-limiting examples of suitable and preferred alkanes are listed above.

The general structural formula of N-mercaptoalkyl-2-pyrrolidones, which are useful as solvents in the process of this invention, is

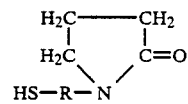

wherein R is a radical selected from the group consisting of —CH$_2$—, —CH$_2$—CH$_2$—, —CH$_2$—CH$_2$—CH$_2$—, —CH(CH$_3$)—CH$_2$—, —CH$_2$—CH(CH$_3$)—, —CH(CH$_3$)—CH(CH$_3$)—, —C(CH$_3$)$_2$—CH(CH$_3$)—, —CH$_2$—CH$_2$—CH$_2$—CH$_2$—, —CH$_2$—CH$_2$—CH$_2$—CH$_2$—CH$_2$—, and the like, and mixtures thereof. The preferred radical R is —CH$_2$—CH$_2$—. Thus, the preferred solvent is N-(β-mercaptoethyl)-2-pyrrolidone:

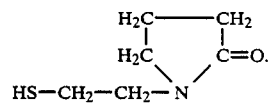

In one preferred embodiment, the solvent contains about 0.1-10 weight-% water, preferably about 2-5 weight-% H$_2$O.

The N-(mercaptoalkyl)-2-pyrrolidones can be prepared by UV-catalyzed addition of H$_2$S to the corresponding N-alkenyl-2-pyrrolidone. For instance, N-(β-mercaptoethyl)-2-pyrrolidone is prepared by reaction of $H_2S$ and N-vinyl-2-pyrrolidone, at room temperature (about 25° C.) and a molar ratio of $H_2S$ to N-vinyl-2-pyrrolidone of about 5-6:1, while the reaction mixture is continuously stirred and subjected to UV radiation. for about 4-6 hours. The formed product, N-(β-mercaptoethyl)-2-pyrrolidone (boiling point: 266° C. at 1 atm; 100° C. at 0.3 mm Hg), is separated from unreacted N-vinylpyrrolidone by fractional distillation.

Any suitable weight ratio of the solvent to the hydrocarbon containing feed mixture can be employed. Preferably, the solvent to feed weight ratio is in the range of from about 0.5:1 to about 50:1, more preferably from about 3:1 to about 20:1.

Any suitable reflux ratio (i.e., the weight ratio of the portion of condensed vapor which is returned to the distillation column to the portion of condensed vapor which is withdrawn as distillate) can be employed in the process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the column. Any suitable pressure can be employed during the extractive distillation. Generally the pressure is about 5 to about 100 psig, preferably about 8 to about 20 psig.

When the feed comprises cycloalkane and alkanes, the overhead distillate (withdrawn from the top of the column) generally contains a smaller volume percentage of cycloalkanes (preferably cyclohexane) than the feed and a larger volume percentage of alkanes (preferably isoalkanes) than the feed. Generally, the bottoms product (a portion of which can be reheated and recycled to the lower portion of the column) contains more of the cycloalkane than the feed, and less of the alkanes (preferably isoalkanes) than the feed. Furthermore, the bottoms product contains essentially all of the added solvent, which can be separated from the other bottoms product components by distillation or other suitable separating means and then be recycled to the extractive distillation column.

When the feed comprises aromatic hydrocarbons and alkanes, the overhead distillate generally contains a smaller volume percentage of aromatic hydrocarbons and a larger volume percentage of alkanes than the feed. Generally, the bottoms product contains more of the aromatic hydrocarbons than the feed, and less of the alkanes than the feed. The bottom product contains substantially all of the added solvent, and can be separated and recycled, as described above.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising naphthenic and paraffinic hydrocarbons is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in paraffinic hydrocarbons (alkanes) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in paraffinic hydrocarbons and a bottoms stream predominantly comprising the naphthenic hydrocarbons and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising naphthenic hydrocarbons is withdrawn from an upper portion of distillation column 29 through conduit 30. This overhead stream can be at least partially condensed in condenser 22. A portion of the overhead stream withdrawn from condenser 32 can be returned through conduit 34 as reflux for distillation column 29, with the remainder of the overhead stream being withdrawn as product, i.e., naphthenic compounds (preferably cyclohexane) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The above process description, which refers to FIG. 1, can also be applied to another preferred embodiment of this invention wherein the feed comprises aromatic and paraffinic hydrocarbons. When this aromatic/paraffinic feed mixture is used, the term "naphthenic", as it appears in the above description (referring to FIG. 1), is replaced by the term "aromatic". The preferred aromatic hydrocarbons which exit through conduit 36 are benzene, toluene and xylenes.

Liquid-Liquid Extraction

Any suitable liquid feed which contains aromatic hydrocarbons containing 6–18 (preferably 6–10) carbon atoms per molecule and alkanes containing 5–20 (preferably 5–10) carbon atoms per molecule can be used in the first liquid-liquid extraction embodiment of this invention (for separating aromatic hydrocarbons from alkanes). Non-limiting examples, including preferred examples, of suitable aromatic hydrocarbons and alkanes are disclosed above (in the "Extractive Distillation" section). Generally the feed has a boiling point (at 1 atm.) in the range of from about 80° to about 500° F., more preferably about 100°–300° F. Generally, the feed contains about 1–90 weight-% aromatic hydrocarbons and about 10–99 weight-% alkanes, preferably about 5–60 weight-% aromatic hydrocarbons and about 40–95 weight-% alkanes.

Any suitable liquid feed which contains cycloalkanes containing 6–18 (preferably 6–10) carbon atoms per molecule and alkanes containing 5–20 (preferably 5–10) carbon atoms per molecule can be used in the second liquid-liquid extraction embodiment of this invention (for separating cycloalkanes from alkanes). Non-limiting examples, including preferred examples, of suitable cycloalkanes and alkanes are disclosed above (in the "Extractive Distillation" section). Generally, the feed has a boiling point (at 1 atm.) in the range of from about 60° to about 500° F., preferably about 100°–300° F. Generally, the feed contains about 1–90 weight-% cycloalkanes and about 10–99 weight-% alkanes, preferably about 5–60 weight-% cycloalkanes and about 40–95 weight-% alkanes.

The solvent (extractant) can be any of the N-mercaptoalkyl-2-pyrrolidones, described above (in the "Extractive Distillation" section). The preferred solvent is N-($\beta$-mercaptoethyl)-2-pyrrolidone. In a preferred embodiment, the solvent additionally contains about 0.1 to about 10-weight-% $H_2O$, more preferably about 1–6 weight-% $H_2O$.

The liquid-liquid extraction process of this invention can be carried out in any manner by any suitable means in any suitable apparatus, as is well known to those having ordinary skill in the art of liquid-liquid extraction. Common liquid-liquid extraction equipment and techniques are described in an article entitled "The Essentials of Extraction" by Jimmy L. Humphrey et al., Chemical Engineering, Sept. 17, 1984, pages 76 and 84–87; and in Kirk-Othmer Encyclopedia of Chemical Technology, Third Edition, Volume 9, 1980, John Wiley and Sons, pages 672–716. Particularly preferred in the process of this invention are continuous liquid-liquid extraction columns such as Scheibel columns and rotating disc columns through which feed and extractant (solvent) are continuously passed in a countercurrent mode of operation, so as to achieve intimate contact of the feed phase and the extractant phase, which are substantially immiscible. The extractant is generally introduced near the top of the extractor column and flows downward, whereas the hydrocarbon-containing feed is introduced near the bottom of the extractor column and flows upward. The raffinate (i.e., the phase which has been extracted and has a lower aromatics or cycloalkane concentration than the feed) generally exits at the top of the column (above the extractant entry point), whereas the extract (i.e., the extractant and the extracted aromatics components of the feed) generally exits at the bottom of the column (below the feed entry point).

Any suitable extraction conditions can be employed. Generally, the temperature during the extraction is about 40° to about 350° F. (preferably about 60°–200° F.), and the pressure is about 1 to 30 atmospheres (preferably about 1 atm.). For the separation of aromatics from alkanes, the weight ratio of extractant to hydrocarbn-containing feed during the extraction process generally is in the range of about 0.1:1 to about 10:1, preferably about 0.5:1 to about 5:1. For the separation of cycloalkanes from alkanes, the weight ratio of solvent to hydrocarbon-containing feed generally is in the range of from about 0.1:1 to about 20:1, preferably about 0.5:1 to about 15:1. The flow rates of feed and extractant, the residence time of both phases in the extractor and other process parameters will greatly depend on the size and shape of the extraction equipment, on the feed viscosity, on desired extraction efficiency and the like, and can be determined by those skilled in the art for particular applications.

The raffinate and extract phases are separated from one another by any conventions means, such as in the above-described column operations. The extract phase generally is passed through a heated stripper where the aromatics (or cycloalkanes) are distilled off and, thus, separated from the higher boiling solvent. The extractant (solvent) is generally recycled to the extractor and reused in the liquid-liquid extraction of the feed. The solvent-free extract can be used as source of aromatics (or cycloalkanes), which may be employed as reactants in industrial processes.

The following examples are presented to further illustrate the invention and are not to be considered unduly limiting the scope of this invention.

EXAMPLE I

This example demonstrates the superiority of N-(β-mercaptoethyl)-2-pyrrolidone (NMEP) versus N-methyl-2-pyrrolidone (NMP) as extractant in an extractive distillation process. NMEP had been prepared in the R & D department of Phillips Petroleum Company, Bartlesville, Okla., by the reaction of N-vinyl-2-pyrrolidone and $H_2S$, as has been described above.

To a hydrocarbon mixture of 85 weight percent cyclohexane and 15 weight percent 2,4-dimethylpentane (2,4-DMP) was added an extractive solvent (either NMPE or NMP) at a solvent:feed weight ratio of 5:1 to 7:1. The total mixture (including the extractive solvent) was heated under reflux conditions for about 20-30 minutes in a distillation flask equipped with a reflux condenser. Then a small sample was withdrawn by means of a septum from the flask containing the liquid phase of the eqilibrium system, and a sample of the condensed vapor was withdrawn by means of a septum located just below the reflux condenser. Both samples were analyzed, and the mole fractions of 2,4-DMP and cyclohexane in the liquid phase and in the condensed vapor phase were determined. The relative volatility R was calculated as follows:

$$R = \frac{Y1/Y2}{X1/X2} = \frac{Y1/X1}{Y2/X2}$$

wherein Y1 and Y2 are the mole fractions of 2,4-DMP and cyclohexane respectively, in the vapor phase, and X1 and X2 are the mole fractions of 2,4-DMP and cyclohexane, respectively, in the liquid phase. Test results are summarized in Table I.

TABLE I

| Added Solvent | Solvent:Feed Weight Ratio | Relative Volatility R |
| --- | --- | --- |
| NMEP | 3:1 | 1.34 |
| NMP | 3:1 | 1.11 |
| NMEP | 5:1 | 1.56 |
| NMP | 5:1 | 1.26 |
| NMEP | 7:1 | 1.76 |
| NMP | 7:1 | 1.32 |

Test data in Table I clearly indicate that N-(β-mercaptoethyl)-2-pyrrolidone would be a more effective solvent (extractant) than N-methyl-2-pyrrolidone in the extractive distillation of a feed comprising cyclohexane and a close-boiling isoalkane(s).

EXAMPLE II

This example illustrates the superiority as solvent of N-(β-mercaptoethyl)-2-pyrrolidone (NMEP) over N-methyl-2-pyrrolidone (NMP) in the extractive distillation of a hydrocarbon mixture of 60 weight-% toluene and 40 weight-% n-heptane. The apparatus described in Example I was used for measuring relaive volatilities:

$$R^1 = \frac{Y3/Y4}{X3/X4} = \frac{Y3/X3}{Y4/X4}$$

wherein Y3 and Y4 are the mole fractions of n-heptane and toluene, respectively, in the vapor phase, and X3 and X4 are the mole fractions of n-heptane and toluene, respectively, in the liquid phase. Test results are summarized in Table II. The solvent:feed weight ratio was 1:1 in all tests. Two liquid phases were present in runs 1-3; only one liquid phase was present in runs 4-6.

TABLE II

| Run | Added Solvent | Wt-% $H_2O$ in Solvent | Temp. (°F.) | Relative Volatility $R^1$ |
| --- | --- | --- | --- | --- |
| 1 | NMEP | 0 | 222 | 3.0 |
| 2 | NMEP | 2 | 217 | 3.2 |
| 3 | NMEP | 4 | 220 | 3.2 |
| 4 | NMP | 0 | 234 | 2.6 |
| 5 | NMP | 2 | 224 | 2.7 |
| 6 | NMP | 4 | 215 | 2.8 |

Test data in Table II indicate that N-(β-mercaptoethyl)-2-pyrrolidone would be more effective than N-methyl-2-pyrrolidone as solvent in the extractive distillation of a feed comprising toluene and a close-boiling paraffin. These data also indicate that the presence of relatively small amounts of water, e.g., about 2-4 weight-% $H_2O$, in the solvent would be beneficial for enhancing the relative volatility and for lowering the boiling temperature (thus lowering the operating temperature).

EXAMPLE III

A feed mixture of 50 weight-% n-heptane and 50 weight-% toluene was extracted at about 74° F. with NMEP or NMP, with or without water, at a feed to extractant weight ratio of 1:1. The extraction was carried out for several hours in a separatory funnel under constant agitation to allow phase equilibrium. Then the agitation was stopped and the two formed phases were allowed to settle. Thereafter, the solvent-rich extract phase and the raffinate phase, from which toluene had been extracted, were separated. This operation is equivalent to one theoretical stage.

Test results are summarized in Table III. Extract and raffinate were analyzed, and the selectivity α was determined by dividing $$\frac{\text{toluene concentration in extract}}{\text{heptane concentration in extract}} \text{ by}$$

$$\frac{\text{toluene concentration in raffinate}}{\text{heptane concentration in raffinate}}.$$

TABLE III

| Solvent | Water in Solvent (Wt. %) | Extract Composition (Wt. %) | | Raffinate Composition (Wt. %) | | Selectivity α |
| --- | --- | --- | --- | --- | --- | --- |
| | | n-Heptane | Toluene | n-Heptane | Toluene | |
| NMEP | 0 | 27.35 | 72.65 | 68.79 | 31.21 | 5.85 |
| NMEP | 3 | 18.52 | 81.48 | 64.79 | 35.21 | 8.10 |
| NMEP | 5 | 15.35 | 84.66 | 62.77 | 37.23 | 9.30 |
| NMP | 0 | (completely miscible with hydrocarbon feed) | | | | |
| NMP | 3 | 40.42 | 59.58 | 70.84 | 29.16 | 3.58 |

TABLE III-continued

| Solvent | Water in Solvent (Wt. %) | Extract Composition (Wt. %) | | Raffinate Composition (Wt. %) | | Selectivity $\alpha$ |
| --- | --- | --- | --- | --- | --- | --- |
| | | n-Heptane | Toluene | n-Heptane | Toluene | |
| NMP | 5 | 30.66 | 69.34 | 68.33 | 31.67 | 4.88 |

Test results Table III clearly show that NMEP was considerably more effective than NMP in extracting the aromatic hydrocarbon (toluene) from the feed. Data in Table III further demonstrate the beneficial effect of water (3-5 weight-% H$_2$O) in the aromatics extraction.

Reasonable variations, modifications and adaptations for various usages and conditions can be made within the scope of the disclosure and the appended claims, without departing from the scope of this invention.

That which is claimed is:

1. In a process for separating at least one cycloalkane containing 5-10 carbon atoms per molecule from at least one close-boiling alkane by extractive distillation of a feed consisting essentially of said at least one cycloalkane and said at least one alkane, the improvement which comprises employing a solvent consisting essentially of at least one N-mercaptoalkyl-2-pyrrolidone alone or in admixture with about 0.1-10 weight-% water, wherein the mercaptoalkyl group in said N-mercaptoalkyl-2-pyrrolidone contains 1-5 carbon atoms;
    wherein said extractive distillation process produces (i) an overhead distillate product which contains a smaller volume percentage of said at least one cycloalkane and a larger volume percentage of said at least one alkane than said feed, and (ii) a bottom product which contains said solvent and a larger volume percentage of said at least one cycloalkane and a smaller volume percentage of said at least one alkane than said feed; and wherein said at least one cycloalkane is separated from said solvent and recovered from said bottoms product.

2. A process in accordance with claim 1, wherein said at least one N-mercaptoalkyl-2-pyrrolidone is N-($\beta$-mercaptoethyl)-2-pyrrolidone.

3. A process in accordance with claim 2, wherein said N-($\beta$-mercaptoethyl)-2-pyrrolidone is admixed with about 2-5 weight-% water.

4. A process in accordance with claim 1, wherein said at least one cycloalkane is cyclohexane.

5. A process in accordance with claim 1, wherein the weight ratio of said solvent to said feed is in the range of from about 0.5:1 to about 50:1.

6. A process in accordance with claim 1, wherein said feed boils at a temperature in the range of from about 80° F. to about 350° F., at a pressure of about 1 atm.

7. A process in accordance with claim 1, wherein the boiling point of said at least one cycloalkane and the boiling point of said at least one alkane differ about 0.2 to about 10° F., at a pressure of about 1 atm.

8. In a process for separating at least one aromatic hydrocarbon containing 6-10 carbon atoms per molecule from at least one close-boiling alkane by extractive distillation of a feed consisting essentially of said at least one aromatic hydrocarbon and said at least one alkane, the improvement which comprises employing a solvent consisting essentially of at least one N-mercaptoalkyl-2-pyrrolidone alone or in admixture with about 0.1-10 weight-% water, wherein the mercaptoalkyl group in said N-mercaptoalkyl-2-pyrrolidone contains 1-5 carbon atoms;
    wherein said extractive distillation process produces (i) an overhead distillate product which contains a smaller volume percentage of said at least one aromatic hydrocarbon and a larger volume percentage of said at least one alkane than said feed, and (ii) a bottoms product which contains said solvent and a larger volume percentage of said at least one aromatic hydrocarbon and a smaller volume percentage of said at least one alkane than said feed; and wherein said at least one aromatic hydrocarbon is separated from said solvent and recovered from said bottoms product.

9. A process in accordance with claim 8, wherein said at least one N-mercaptoalkyl-2-pyrrolidone is N-($\beta$-mercaptoethyl)-2-pyrrolidone.

10. A process in accordance with claim 9, wherein said N-($\beta$-mercaptoethyl)-2-pyrrolidone is admixed with about 2-5 weight-% water.

11. A process in accordance with claim 8, wherein said at least one aromatic hydrocarbon is selected from the group consisting of benzene, toluene, p-xylene, m-xylene and o-xylene.

12. A process in accordance with claim 8, wherein the weight ratio of said solvent to said feed is in the range of from about 0.5:1 to about 50:1.

13. A process in accordance with claim 8, wherein said feed boils at a temperature in the range of from about 80° F. to about 350° F., at a pressure of about 1 atm.

14. A process in accordance with claim 8, wherein the boiling point of said at least one aromatic hydrocarbon and the boiling point of said at least one alkane differ about 0.2 to about 10° F., at a pressure of about 1 atm.

15. In a process for separating at least one aromatic hydrocarbon containing 6-18 carbon atoms per molecule from at least one alkane containing 5-20 carbon atoms per molecule by liquid-liquid extraction of a feed consisting essentially of said at least one aromatic hydrocarbon and said at least one alkane, the improvement which comprises employing a solvent consisting essentially of at least one N-mercaptoalkyl-2-pyrrolidone alone or in admixture with about 0.1-10 weight-% water, wherein the mercaptoalkyl group in said N-mercaptoalkyl-2-pyrrolidone contains 1-5 carbon atoms per molecule;
    wherein an extract phase is formed which comprises said solvent and at least a portion of said at least one aromatic hydrocarbon, and a raffinate phase is formed in which the concentration of said at least one aromatic hydrocarbon is lower than in said feed.

16. A process in accordance with claim 15, wherein said at least one N-mercaptoalkyl-2-pyrrolidone is N-($\beta$-mercaptoethyl)-2-pyrrolidone.

17. A process in accordance with claim 16, wherein said N-($\beta$-mercaptoalkyl)-2-pyrrolidone is admixed with about 1-6 weight-% water.

18. A process in accordance with claim 15, wherein said feed contains about 1-90 weight-% aromatic hydrocarbons.

19. A process in accordance with claim 15, wherein said at least one aromatic hydrocarbon contains about 6-10 carbon atoms per molecule.

20. A process in accordance with claim 15, wherein said at least one aromatic hydrocarbon is selected from the group consisting of benzene, toluene, p-xylene, m-xylene and o-xylene.

21. A process in accordance with claim 15, wherein said at least one N-mercaptoalkyl-2-pyrrolidone is N-(β-mercaptoethyl)-2-pyrrolidone, and said at least one aromatic hydrocarbon is selected from the group consisting of benzene, toluene, p-xylene, m-xylene and o-xylene.

22. A process in accordance with claim 21, wherein said N-(β-mercaptoethyl)-2-pyrrolidone is admixed with about 1-6 weight-% water.

23. A process in accordance with claim 15, wherein said liquid-liquid extraction is carried out at a temperature of about 40°-350° F. and a weight ratio of said solvent to said feed of about 0.1:1 to about 10:1.

24. In a process for separating at least one cycloalkane containing 6-18 carbon atoms per molecule from at least one alkane containing 5-20 carbon atoms per molecule by liquid-liquid extraction of a feed consisting essentially of said at least one cycloalkane and said at least one alkane, the improvement which comprises employing a solvent consisting essentially of at least one N-mercaptoalkyl-2-pyrrolidone alone or in admixture with about 0.1-10 weight-% water, wherein the mercaptoalkyl group in said N-mercaptoalkyl-2-pyrrolidone contains 1-5 carbon atoms per molecule;

wherein an extract phase is formed which comprises said solvent and at least a portion of said at least one cycloalkane, and a raffinate phase is formed with the concentration of said at least one cycloalkane is lower than in said feed.

25. A process in accordance with claim 24, wherein said at least one N-mercaptoalkyl-2-pyrrolidone is N-(β-mercaptoethyl)-2-pyrrolidone.

26. A process in accordance with claim 25, wherein said N-(β-mercaptoethyl)-2-pyrrolidone is admixed with about 1-6 weight-% water.

27. A process in accordance with claim 24, wherein said feed contains about 1-90 weight-% cycloalkanes.

28. A process in accordance with claim 24, wherein said liquid-liquid extraction is carried out at a temperature of about 40°-350° F. and a weight ratio of said solvent to said feed of about 0.1:1 to about 20:1.

* * * * *